(12) United States Patent
Jacobsen

(10) Patent No.: US 10,786,628 B2
(45) Date of Patent: Sep. 29, 2020

(54) DEFORMABLE PISTON WASHER

(71) Applicant: Novo Nordisk A/S, Bagsvaerd (DK)

(72) Inventor: Nikolaj Eusebius Jacobsen, Soeborg (DK)

(73) Assignee: Novo Nordisk A/S, Bagsvaerd (DK)

(*) Notice: Subject to any disclaimer, the term of this patent is extended or adjusted under 35 U.S.C. 154(b) by 457 days.

(21) Appl. No.: 15/560,257

(22) PCT Filed: Mar. 4, 2016

(86) PCT No.: PCT/EP2016/054693
§ 371 (c)(1),
(2) Date: Sep. 21, 2017

(87) PCT Pub. No.: WO2016/155975
PCT Pub. Date: Oct. 6, 2016

(65) Prior Publication Data
US 2018/0064878 A1    Mar. 8, 2018

(30) Foreign Application Priority Data
Mar. 27, 2015 (EP) .................................... 15161256

(51) Int. Cl.
*A61M 5/31* (2006.01)
*A61M 5/315* (2006.01)

(52) U.S. Cl.
CPC . *A61M 5/31515* (2013.01); *A61M 2205/3372* (2013.01); *A61M 2205/583* (2013.01)

(58) Field of Classification Search
CPC .... A61M 2205/3372; A61M 2205/583; A61M 5/31515
See application file for complete search history.

(56) References Cited

U.S. PATENT DOCUMENTS

| 4,145,918 A | 3/1979 | Couch et al. |
| 4,191,125 A | 3/1980 | Johnson |

(Continued)

FOREIGN PATENT DOCUMENTS

| CN | 101217989 A | 7/2008 |
| CN | 101227943 A | 7/2008 |

(Continued)

*Primary Examiner* — Imani N Hayman
(74) *Attorney, Agent, or Firm* — Wesley Nicolas

(57) ABSTRACT

The present invention provides a piston washer (1, 51) for a drug delivery device, the piston washer (1, 51) comprising a central portion (2, 72) arranged about a centre axis, a peripheral portion (3, 73), and an axially pliable structure (8, 78) connecting the central portion (2, 72) and the peripheral portion (3, 73). The axially pliable structure (8, 78) is preconfigured to undergo permanent deformation in response to a difference between a first resultant force acting on the peripheral portion (3, 73) and a second resultant force acting on the central portion (2, 72) exceeding a threshold level. The piston washer (1, 51) is configured to transition permanently by deformation of the axially pliable structure (8, 78) from a first state in which the central portion (2, 72) and the peripheral portion (3, 73) are physically connected and assume a first relative axial position to a second state in which the central portion (2, 72) and the peripheral portion (3, 73) are physically connected and assume a second relative axial position in response to the difference between the first resultant force and the second resultant force transiently exceeding the threshold level.

13 Claims, 5 Drawing Sheets

(56) References Cited

U.S. PATENT DOCUMENTS

| | | | |
|---|---|---|---|
| 6,235,004 | B1 | 5/2001 | Steenfeldt-Jensen et al. |
| 7,415,939 | B2 | 8/2008 | Dip |
| 8,920,383 | B2 | 12/2014 | Enggaard et al. |
| 9,732,851 | B2 * | 8/2017 | Kiilerich .................. F16J 1/005 |
| 2002/0007147 | A1 | 1/2002 | Capes et al. |
| 2008/0082055 | A1 | 4/2008 | Lloyd et al. |
| 2012/0238950 | A1 | 9/2012 | Milan |
| 2014/0116246 | A1 | 5/2014 | Melander |
| 2015/0038917 | A1 | 2/2015 | Nielsen |

FOREIGN PATENT DOCUMENTS

| | | |
|---|---|---|
| DE | 102004059126 A1 | 6/2006 |
| EP | 774268 A1 | 5/1997 |
| EP | 2010847 A2 | 1/2009 |
| JP | 2004-092671 A | 3/2004 |
| JP | 2006500161 | 1/2006 |
| JP | 2008-307237 A | 12/2008 |
| WO | 2007068061 A1 | 6/2007 |
| WO | 2010139641 A1 | 12/2010 |
| WO | 2011003979 A1 | 1/2011 |
| WO | 2011/042539 A1 | 4/2011 |
| WO | 2011039226 A1 | 4/2011 |
| WO | 2012143494 A1 | 10/2012 |
| WO | 2013034467 A1 | 3/2013 |
| WO | 14099831 A2 | 6/2014 |

* cited by examiner (a)          (b)

(a)          (b)

DEFORMABLE PISTON WASHER

CROSS-REFERENCE TO RELATED APPLICATIONS

This application is a 35 U.S.C. § 371 National Stage application of International Application PCT/EP2016/054693 (published as WO 2016/155975), filed Mar. 4, 2016, which claims priority to European Patent Application 15161256.1, filed Mar. 27, 2015; the contents of which are incorporated herein by reference.

FIELD OF THE INVENTION

The present invention relates to drug delivery devices and components for such devices.

BACKGROUND OF THE INVENTION

People suffering from diabetes often have to inject themselves with insulin on a daily basis. Over the last 30 years a great number of different pen injection systems have been developed to ease the self-administration procedure. Pen injectors typically comprise a cartridge containing a liquid drug to be injected. The cartridge is provided with a piston which is moved forward in order to transfer the liquid drug from the injection pen and into the body of the user through an attached injection needle.

An example of a commercially successful injection pen, the Flexpen® by Novo Nordisk A/S, is provided in U.S. Pat. No. 6,235,004. The cartridge (89) as e.g. depicted in FIG. 15-17 contains the liquid drug to be expelled. At the proximal end the cartridge (89) is closed by a rubber piston which is moved forward inside the cartridge (89) by a piston rod (7). In order to transfer and distribute the force from the piston rod (7) to the rubber piston, a piston washer or piston rod foot (9) is provided between the piston rod (7) and the rubber piston. The piston washer is significantly smaller in diameter than the cartridge interior and the piston sliding inside the cartridge.

For prefilled injection pens which are discarded when the user has used the prefilled amount of drug there is no possibility for the user to return the piston rod to its initial position. The dosing mechanism is usually constructed such that the piston rod can only move in the distal direction since the injection pen is designed only to be used until the prefilled amount of drug has been exhausted. Further, these injection pens are sealed such that the user cannot physically obtain contact with the piston rod. In such injection pens the piston washer is normally lying loosely between the rubber piston and the piston rod without being attached to any of the two components since this is the easiest way to assemble the injection pen.

Many pharmaceutical companies advise that the liquid drug be stored in a refrigerator or another cold storage facility. However, liquid drugs are generally sensible to frost. The liquid drug should therefore be stored above 0° C. at all times. Liquid drugs are often contained in a glass cartridge. If such a glass cartridge is exposed to frost not only will the liquid drug potentially be damaged but the liquid will also expand its volume. The increased pressure arising from the expansion can cause the glass cartridge to fracture if no other possibility for expansion is provided.

WO 2007/068061 (Safety Medical Products Limited) discloses a container for a liquid drug in which the cap can move axially if the drug is exposed to frost.

In a prefilled injection pen, the elastomeric piston cannot move freely in the proximal direction due to the presence of the piston rod. However, if the radial dimension of the piston washer is smaller than the proximal (or rear) surface area of the piston, the peripheral portion of the piston is allowed to move proximally and thereby deform around the piston washer. This reduces the risk of crack formation in the cartridge wall, but introduces a risk of rubber wedging in between the cartridge wall and the piston washer if the distance therebetween is too small. Conventional piston washers therefore have sufficiently small diameters to prevent the piston from getting stuck.

In order to maximise the dose delivery precision many manufacturers of pen injectors advise that the injection needle remains in the skin for at least six seconds following a finalised dose administration. This is i.a. to give the piston time to relax and resume its normal unstrained state, a process which inevitably leads to an additional expelling of a small volume of the drug through the injection needle. The at least six seconds of extra time to completion of injection is, however, unsatisfactory from a user perspective, and a minimisation of the accumulated flexibility in the dosing system is accordingly desirable. A small diameter piston washer does not contribute positively to this minimisation.

Due to the friction between the cartridge wall and the piston during dose expelling the maximum precision of the injectable dose is obtained if the pressure from the piston rod is equally distributed across the proximal surface of the piston, and especially also applied as close to the cartridge wall as possible. However, a large diameter of the piston washer, which is required in order to distribute the force from the piston rod to the periphery of the piston, will prevent also the peripheral portion of the piston from moving in the proximal direction when exposed to frost, and will thereby increase the risk of breakage of the glass.

WO 2013/034467 (Novo Nordisk A/S) discloses a drug delivery apparatus with a piston washer comprising a centre part and an outer part which are structured to detach from one another when a force above a certain threshold limit is applied to the outer part. During a normal dose administration the force from the piston rod may thereby be distributed across the entire proximal piston surface, reducing the amount of deformation of the piston and thus the time for subsequent relaxation thereof, while an excessive proximally directed pressure from the piston due to an exposure of the drug delivery apparatus to frost will cause the two piston washer parts to detach, thereby reducing the risk of crack formation as well as providing a clear indication that the device and/or the content of the cartridge may be damaged.

Even if the liquid drug is not damaged by an exposure to frost the entire drug volume will be wasted if the delivery device is either damaged or perceived as damaged and the cartridge cannot be transferred to another delivery device. While the solution presented in WO 2013/034467 provides obvious advantages over the prior art the fact that the peripheral part of the piston washer separates from the centre part and therefore as such becomes an unsupported element in the drug delivery device may potentially confuse a user and lead her/him into concluding that the device is malfunctioning, even though its core functions are intact and the device actually is fully functional.

SUMMARY OF THE INVENTION

It is an object of the invention to eliminate or reduce at least one drawback of the prior art, or to provide a useful alternative to prior art solutions.

In particular, it is an object of the invention to provide a piston washer for a drug delivery device, which piston washer enables a reduction of the time for relaxation of the piston following a dose administration, e.g. while allowing the drug in the reservoir to expand without causing, or seemingly causing, a device malfunction.

It is a further object of the invention to provide a piston washer which can be used as a frost indicator for a drug delivery device.

It is an even further object of the invention to provide such a piston washer which is inexpensive to produce, thereby adding only little to the production costs of a drug delivery device incorporating the piston washer.

It is also an object of the invention to provide an injection device having a reduced relaxation time compared to currently marketed injection devices, as well as a clearly functioning dose delivery mechanism following exposure of the injection device to frost.

In the disclosure of the present invention, aspects and embodiments will be described which will address one or more of the above objects and/or which will address objects apparent from the following text.

A piston washer embodying the principles of the invention comprises a central portion arranged about a centre axis, and a peripheral portion, and the piston washer is capable of transitioning controllably from a first state in which the peripheral portion and the central portion are physically connected and assume a first relative axial position to a second state in which the peripheral portion and the central portion are physically connected and assume a second relative axial position. This allows for the production of a drug delivery device having a piston washer of the same, or substantially the same, diameter as the piston in the drug container, whereby a pressure from the piston rod on the piston washer may be distributed across the entire, or substantially the entire, proximal surface of the piston, reducing the time of relaxation of the piston following a dose administration, while at the same time the piston washer is able to deform by displacement of the peripheral portion relative to the central portion, enabling a volume expansion of the drug substance (with an accompanying peripheral deformation of the piston) that does not cause the container wall to break. During a transition from the first state to the second state the peripheral portion may be permanently axially displaced relative to the central portion, providing a lasting visible indication of the transition.

Accordingly, in one aspect of the invention, a piston washer for a drug delivery device is provided, the piston washer comprising a central portion arranged, e.g. at least substantially axisymmetrically, about a longitudinal axis, a peripheral portion, and an axially deformable structure connecting the central portion and the peripheral portion, the axially deformable structure being preconfigured, i.e. designed specifically, to deform permanently, e.g. before any other area of the piston washer, in response to a difference between a first resultant force acting on the peripheral portion and a second resultant force acting on the central portion exceeding a threshold level. The axially deformable structure thus constitutes a weakened area and provides for a controlled relative axial displacement between the peripheral portion and the central portion. The axially deformable structure may be configured to exhibit plastic deformation.

Further, the piston washer is configured to transition from a first state in which the peripheral portion and the central portion are physically connected and assume a first relative position along the longitudinal axis to a second state in which the peripheral portion and the central portion are physically connected and assume a second relative position along the longitudinal axis, by deformation of the axially deformable structure, in response to the difference between the first resultant force and the second resultant force exceeding the threshold level. Following the transition from the first state to the second state, when the difference between the first resultant force and the second resultant force falls to or below the threshold level the peripheral portion is permanently axially displaced relative to the central portion.

In other words, the central portion and the peripheral portion remain physically connected during the transition of the piston washer from the first state to the second state. Thereby, when in use no detached portion of the piston washer will move around freely in the drug delivery device at any time, potentially causing concerns as to the dose accuracy of the device. The permanent axial displacement of the peripheral portion relative to the central portion enables a user to visually inspect the current state of the piston washer and thereby get an indication of whether the piston has been transiently deformed and thereby whether the drug delivery device has been exposed to frost.

The central portion may comprise a proximal surface adapted for abutment or engagement with a piston rod in the drug delivery device and a distal surface adapted for abutment with a central piston portion. The peripheral portion may comprise an annular member arranged concentrically about the central portion, the annular member comprising a distal surface adapted for abutment with a peripheral piston portion. In particular, the central portion may have a circular, or substantially circular, configuration, such as a disc configuration, and the peripheral portion may have a circular, or substantially circular, ring configuration. This provides for symmetry in the construction which in combination with the axisymmetrical load distribution from the piston rod, the piston and the container wall ensures an at least substantially axisymmetrical deformation of the piston washer. It is noted that the annular member may be unitary or segmented, i.e. the annular member need not be formed as a single piece, but may comprise circumferentially spaced apart curved pieces. These curved pieces may be separate or interconnected.

The piston washer may have a total transversal dimension (i.e. perpendicularly to the longitudinal axis), and the central portion may have a central transversal dimension which is at least 50% of the total transversal dimension. This ensures that if the piston washer becomes permanently deformed, e.g. due to drug freezing, then there is still a sufficiently large contact area between the piston washer and the piston when the drug has thawed to which the force from the piston rod can be distributed without the precision of the drug administration being compromised.

Ideally, the central portion has a central transversal dimension which is at least 50% and at most 80% of the total transversal dimension to thereby also reduce the risk of piston wedging.

In some embodiments of the invention the axially pliable structure comprises a telescopic tube arranged between the central portion and the peripheral portion. An interior portion of a first tube segment is axially fixed to a radially outwardly directed surface of the central portion, while an exterior portion of a second tube segment is axially fixed to a radially inwardly directed surface of the peripheral portion, and a resistance to relative axial motion between the two tube segments is chosen such that relative axial motion only occurs when the difference between the first resultant force acting on the peripheral portion and the second resultant force acting on the central portion exceeds the threshold level.

In particular embodiments of the invention the central portion and the peripheral portion are radially separated, and the axially pliable structure constitutes a radially extending deformation zone connecting the central portion and the peripheral portion. For example, the axially pliable structure may comprise a plurality of radial bridges which each comprises a first end being connected to a radially inwardly directed surface of the peripheral portion and a second end being connected to a radially outwardly directed surface of the central portion.

The plurality of radial bridges may be evenly distributed along a circumference of the central portion to maintain an axisymmetrical construction. The specific number of radial bridges as well as their respective form may be chosen such that permanent relative axial displacement between the peripheral portion and the central portion only occurs when the difference between the first resultant force acting on the peripheral portion and the second resultant force acting on the central portion exceeds the threshold level.

As another example, the axially pliable structure may comprise a round-going collar connecting the central portion and the peripheral portion. This collar may be structured to deform before any area of the central portion and the peripheral portion when the difference between the first resultant force acting on the peripheral portion and the second resultant force acting on the central portion exceeds the threshold level.

The axially pliable structure may, for example, be made of, or at least substantially comprise, polypropylene or polyethylene. In particular, the constituent material may be a PP block copolymer such as SABIC® PP58MNK10.

In particular embodiments of the invention the central portion, the peripheral portion and the axially pliable structure are of the same material, thus providing a fully contained single component solution. A single component piston washer as disclosed herein can be manufactured at a low cost.

The central portion and the peripheral portion may, respectively, have a greater thickness than the axially pliable structure in order to ensure that material deformation only occurs, or at least occurs first, in or at the axially pliable structure. Alternatively, or additionally, the axially pliable structure may have a lower yield strength than the central portion and the peripheral portion.

The peripheral portion may comprise a first rim portion and the central portion may comprise a second rim portion which appears visibly different from the first rim portion. For example, the first rim portion may have a first colour or shade and the second rim portion may have a second colour or shade being different from the first colour or shade. This will enhance the visual evidence of a permanent relative displacement between the peripheral portion and the central portion. The first rim portion may be a portion of, or the entire, radially outwardly directed surface of the peripheral portion and the second rim portion may be a portion of, or the entire, radially outwardly directed surface of the central portion.

The radially outwardly directed surface of the peripheral portion may comprise two or more radially outwardly directed protrusions. The protrusions may thus serve as contact interfaces for an internal drug reservoir wall, while the radially outwardly directed surface of the peripheral portion is separated a small distance from the reservoir wall. The protrusions may be distributed equidistantly along the circumference of the peripheral portion to provide an axisymmetrical support of the piston washer in a drug reservoir.

A segment of the peripheral portion may be flexible, e.g. radially deflectable, to allow a small elastic deformation of the piston washer, e.g. in connection with the initial arrangement thereof in a container vessel having an open end of smaller dimensions than the transversal dimension of the container interior.

The first resultant force may be formed by contributions from e.g. frictional forces between an exterior surface of the peripheral portion and the wall of the drug container, a push force from proximal displacement of the piston periphery, and the material properties and/or configurations of the central portion and the axially pliable structure serving to transfer a share of the force from the piston rod to the peripheral portion. The second resultant force may be formed by contributions from e.g. the piston rod and the piston, being subjected to pressure from the contents of the reservoir. Under normal circumstances, e.g. during administration, the difference between the first resultant force and the second resultant force does not exceed the threshold level, and the piston washer does not undergo any permanent deformation. However, under extreme conditions such as an exposure to frost the force from the expanding drug substance in the reservoir will cause the difference between the first resultant force and the second resultant force to increase and eventually pass the threshold level.

In another aspect of the invention a drug delivery device, e.g. an injection device such as a pen injector, comprising a piston washer as described in the above is provided.

For example, an injection device may be provided comprising: a housing extending along a longitudinal axis, a dose expelling mechanism comprising a piston rod extending between a proximal end portion and a distal end portion, and a piston washer comprising a central portion abutting the distal end portion, a peripheral portion, and an axially pliable structure connecting the central portion and the peripheral portion. The axially pliable structure is preconfigured to undergo permanent deformation in response to a proximally directed force on the peripheral portion exceeding a threshold level. The piston rod is configured to shift between a restricted state in which proximal motion (of the piston rod) relative to the housing is prevented and a free state in which proximal motion (of the piston rod) relative to the housing is allowed. The piston washer is configured to transition permanently, by deformation of the axially pliable structure, from a first state in which the central portion and the peripheral portion are physically connected and assume a first relative axial position to a second state in which the central portion and the peripheral portion are physically connected and assume a second relative axial position in response to the proximally directed force on the peripheral portion transiently exceeding the threshold level, when the piston rod is in the restricted state.

In particular, the peripheral portion may be configured to undergo permanent proximal displacement relative to the central portion in response to the proximally directed force on the peripheral portion transiently exceeding the threshold level.

The peripheral portion and the central portion may be connected by a plurality of bridging structures, and the permanent proximal displacement may be realised by plastic deformation of the bridging structures.

As another example, an injection device may be provided comprising: a) a housing, b) a drug container connected with the housing and comprising a chamber defined by a cylindrical container wall extending along a longitudinal axis, a pierceable septum, and an axially slidable piston having a proximal end surface and a distal end surface, and c) a dose expelling mechanism comprising a piston rod configured for unidirectional distal motion relative to the housing, and a piston washer comprising a central portion abutting the piston rod, a peripheral portion, e.g. at least partially contacting the cylindrical container wall, and an axially pliable structure connecting the central portion and the peripheral portion. The piston washer is arranged to abut the proximal end surface of the piston, and the axially pliable structure is preconfigured to undergo permanent deformation in response to a proximally directed force on the distal end surface of the piston exceeding a threshold level. The piston washer is configured to transition permanently, by deformation of the axially pliable structure, from a first state in which the central portion and the peripheral portion are physically connected and assume a first relative axial position to a second state in which the central portion and the peripheral portion are physically connected and assume a second relative axial position in response to the proximally directed force on the distal end surface of the piston transiently exceeding the threshold level.

This may correspond to a situation where a substance in the chamber freezes and undergoes a volume expansion. The proximally directed force on the piston from the expanding substance is resisted by the piston rod which is prevented from proximal motion relative to the housing. The central portion, being situated between the piston and the piston rod, is thus also prevented from proximal motion relative to the housing, leaving the expansion of the chamber to occur near the container wall, as the piston periphery forces the peripheral portion proximally relative to the central portion.

When the substance in the chamber at some point thaws and accordingly retracts the elastic properties of the piston allows it to resume its original shape, but the piston washer is permanently deformed and does thus not resume its initial shape. The time in which the substance is frozen may be short or long, but in the present context as long as the time is finite the force exceeding the threshold level is transient.

The threshold level may be predetermined by the manufacturer, e.g. by choice of material for and/or design of the piston washer. It is noted, however, that the exact threshold level need not be known by the manufacturer as long as it lies within an interval of threshold levels which ensures that at least ordinary distally directed movements of the piston rod during dose expelling will not cause a permanent displacement of the peripheral portion relative to the central portion and that an expansion of the drug substance due to freezing will. Threshold levels meeting this dual requirement may be identified by experimentation.

Elastomeric pistons usable for cartridge carrying drug delivery devices are typically mass produced in bulk batches and are stored end-to-end to minimise storage space. In order to reduce the risk of the individual pistons sticking to the neighbouring pistons in storage, and thereby become difficult to handle when taken into use, some manufacturers choose to shape all the pistons such that the proximal piston ends have one or more protruding geometries, whereby the contact surface between two piston ends is significantly reduced. This, however, presents a downside in respect of the desire to reduce the time of complete relaxation, as conventional piston washers elastically compress such protruding geometries, and/or air trapped between the proximal piston end and the distal piston washer end, during drug expelling, thereby adding to the flexibility of the dosing system.

Thus, in a further aspect of the invention a drug delivery device, such as e.g. an injection device, is provided comprising a piston configured to move in a drug reservoir to expel a volume of drug therefrom, a piston rod for moving the piston, and a piston washer arranged between the piston rod and the piston, wherein the piston comprises a first material having a first hardness and the piston washer comprises a second material having a second hardness, the first material and the second material being arranged in, or arranged to enter into, contact, and wherein the first hardness is greater than the second hardness.

If the second material is softer than the first material in the interface between the piston and the piston washer the piston washer will deform more than the piston when the two are pressed together.

If, in addition, the second material has a high compression set, e.g. of more than 50%, the system comprising the piston and the piston washer will exhibit a significantly reduced elastic recovery and the result is a reduced relaxation time following an expelling of a dose of drug from the reservoir. A material having a compression set in the range of [55%, 75%] appears particularly attractive in this context. An exemplary material is a TPE compound such as Meliflex R22069C, produced by Melitek.

In an even further aspect of the invention a drug delivery device, such as e.g. an injection device, is provided comprising a piston configured to move in a drug reservoir to expel a volume of drug therefrom, a piston rod for moving the piston, and a piston washer arranged between the piston rod and the piston, wherein the piston comprises a first material having a first hardness and a first compression set, and the piston washer comprises a second material having a second hardness and a second compression set, the first material and the second material being arranged in, or arranged to enter into, abutting contact, and wherein the first hardness is greater than the second hardness and the second compression set is greater than the first compression set.

The fact that the second compression set is greater than the first compression set, in combination with first hardness being greater than the second hardness, provides for a construction where the piston washer not only accepts the majority of the total deformation but also sets more than the piston, enhancing the degree to which the piston maintains its original shape during use. In a prefilled injection device, for example, the piston washer may be brought into abutment with the piston during assembly of the device, and the connection between the two may be pressurised, e.g. by providing an excess pressure in the drug reservoir, to give the imprint of the protruding piston geometries on the piston washer sufficient time to settle before the device is used for the first time.

In particular embodiments of the invention a drug delivery device, such as e.g. an injection device, is provided comprising a drug reservoir having a chamber defined by a) a reservoir body, b) a penetrable septum closing a first portion of the reservoir body, and c) a piston closing a second, e.g. opposite, portion of the reservoir body, a piston rod for moving the piston towards the penetrable septum, and a piston washer arranged between the piston rod and the piston. The piston washer comprises a central portion arranged about a centre axis, a peripheral portion, and an axially pliable structure connecting the central portion and the peripheral portion. The axially pliable structure is preconfigured to undergo permanent deformation in response to a difference between a first resultant force acting on the peripheral portion and a second resultant force acting on the central portion exceeding a threshold level. The piston washer is configured to transition permanently by deformation of the axially pliable structure from a first state in which the central portion and the peripheral portion are physically connected and assume a first relative axial position to a second state in which the central portion and the peripheral portion are physically connected and assume a second relative axial position in response to the difference between the first resultant force and the second resultant force transiently exceeding the threshold level. A proximal end portion of the piston comprises a first material having a first hardness and a first compression set, and a distal end portion of the piston washer comprises a second material having a second hardness and a second compression set. The first material and the second material are arranged to be in, or to enter into, abutment. Furthermore, the first hardness is greater than the second hardness, and the second compression set is higher than the first compression set and/or is at least 50%, such as e.g. in the range of [55%, 75%]. As used herein, the terms "distal" and "proximal" denote positions at or directions along a drug delivery device, where "distal" refers to the drug outlet end and "proximal" refers to the end opposite the drug outlet end.

In the present specification, reference to a certain aspect or a certain embodiment (e.g. "an aspect", "a first aspect", "one embodiment", "an exemplary embodiment", or the like) signifies that a particular feature, structure, or characteristic described in connection with the respective aspect or embodiment is included in, or inherent of, at least that one aspect or embodiment of the invention, but not necessarily in/of all aspects or embodiments of the invention. It is emphasized, however, that any combination of the various features, structures and/or characteristics described in relation to the invention is encompassed by the invention unless expressly stated herein or clearly contradicted by context.

The use of any and all examples, or exemplary language (e.g., such as, etc.), in the text is intended to merely illuminate the invention and does not pose a limitation on the scope of the same, unless otherwise claimed. Further, no language or wording in the specification should be construed as indicating any non-claimed element as essential to the practice of the invention.

BRIEF DESCRIPTION OF THE DRAWINGS

In the following the invention will be further described with references to the drawings, wherein.

In the figures like structures are mainly identified by like reference numerals.

DESCRIPTION OF EXEMPLARY EMBODIMENTS

Figure 1:
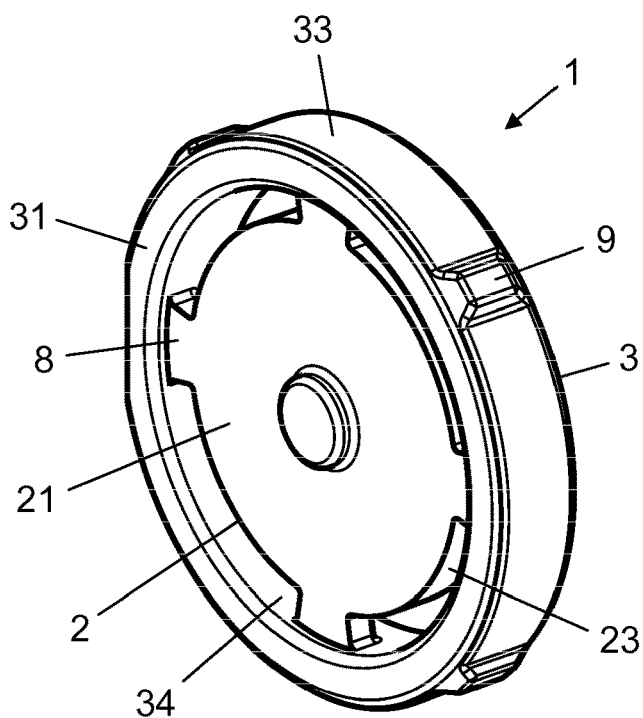
FIGS. 1A and 1B show different views of a piston washer according to an embodiment of the invention before permanent deformation.
Figure 1:
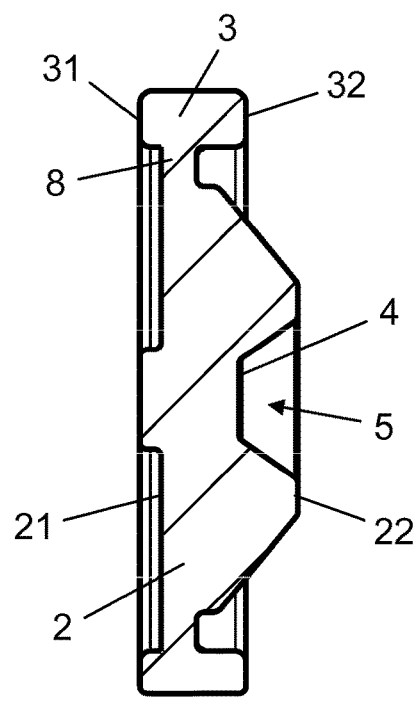

When in the following relative expressions, such as "upper" and "lower", are used, these refer to the appended figures and not necessarily to an actual situation of use. The shown figures are schematic representations for which reason the configuration of the different structures as well as their relative dimensions are intended to serve illustrative purposes only.

FIGS. 1a and 1b are perspective, respectively cross-sectional views of a piston washer 1 according to an exemplary embodiment of the present invention, in an initial state before permanent deformation. The piston washer 1 comprises a centre portion 2 and an outer portion 3 connected by four bridges 8, each of which extend radially between an exterior surface 23 of the centre portion 2 and an interior surface 34 of the outer portion 3. The centre portion 2 has a distal surface 21 adapted to abut a piston (not shown) during use and a proximal surface 22. The proximal surface 22 is provided with a central depression 5 and has a depressed surface 4 adapted to abut a piston rod (not shown) during use. The outer portion 3 has a distal surface 31 adapted to abut the piston during use and a proximal surface 32. The outer portion 3 further has a circumferential exterior surface 33 along which four protrusions 9 (only three are visible) are distributed. When the piston washer 1 is arranged in a drug cartridge only the protrusions 9 are in contact with an interior cartridge wall, not the entire exterior surface 33. The protrusions 9 are distributed equidistantly along the exterior surface 33, providing for a stable centralised positioning of the piston washer 1. Between each pair of protrusions 9 the exterior surface 33 comprises a flexible zone, enabling easy placement of the piston washer 1, also in a drug cartridge having a proximal end portion of slightly smaller diameter than the maximum radial dimension of the piston washer 1.

Figure 2:
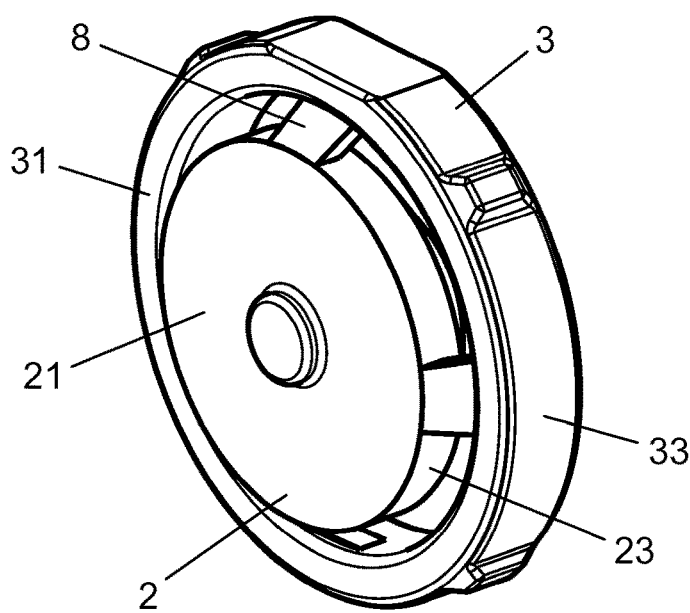
FIGS. 2A and 2B show different views of the piston washer after permanent deformation.
Figure 2:
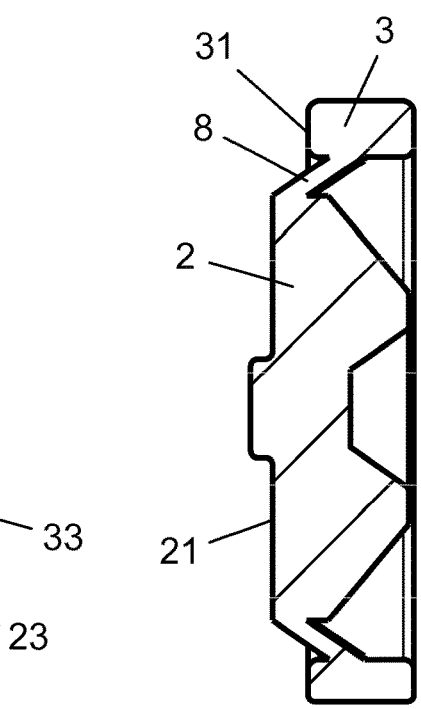

In FIGS. 2a and 2b the piston washer 1 is shown in an exemplary state after permanent deformation has occurred. The bridges 8 have undergone plastic deformation during a proximal displacement of the outer portion 3 relative to the centre portion 2, and as a result the distal surface 31 is now positioned proximally of the distal surface 21.

Figure 3:
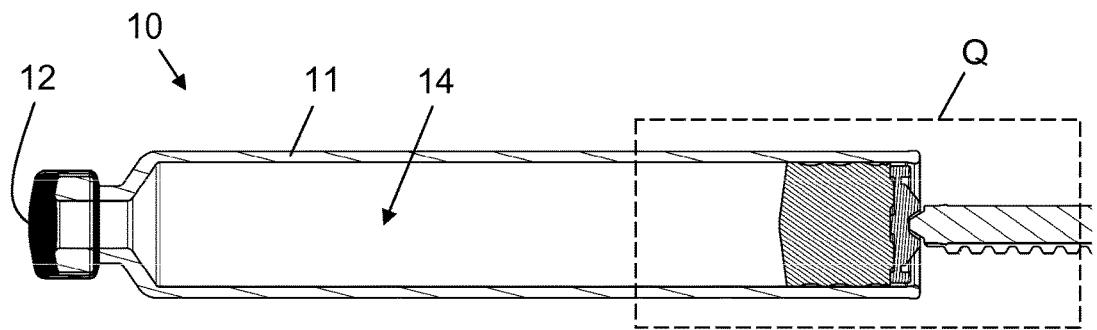
FIG. 3 is a longitudinal cross-section view of the piston washer between a piston rod and a piston in a drug cartridge before permanent deformation of the piston washer.

FIG. 3 is a cross-sectional longitudinal view of a drug cartridge 10 having a generally cylindrical wall 11 and being closed at a distal end by a pierceable rubber septum 12. Opposite thereto a slidable sealing piston 15 (see FIG. 4) is arranged, which together with the septum 12 and the wall 11 defines a closed chamber 14 containing a drug substance (not visible). The cartridge 10 forms part of a drug delivery device (not shown), and is shown in a pre-use state before any drug expelling has taken place.

Figure 4:
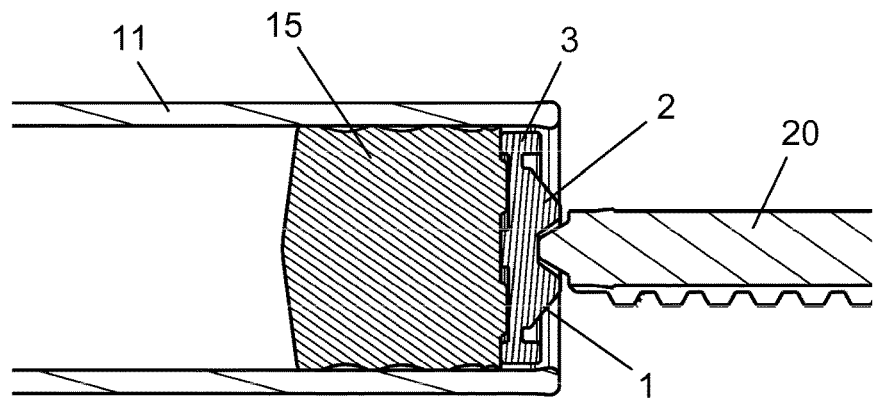
FIG. 4 is a close up of a proximal section of the drug cartridge of FIG. 3.

FIG. 4 is a close up of a proximal section of the cartridge 10 as delimited by the area Q in FIG. 3, showing the piston washer 1 arranged at a proximal end of the wall 11 between the piston 15 and a piston rod 20. It is noted that the piston washer 1 contacts the piston 15 across substantially the entire proximal surface of the piston 15, thereby enabling a distribution of the distally directed force from the piston rod 20 during a dose administration also to a peripheral portion 15A (see FIG. 5) of the piston 15.

Figure 5:
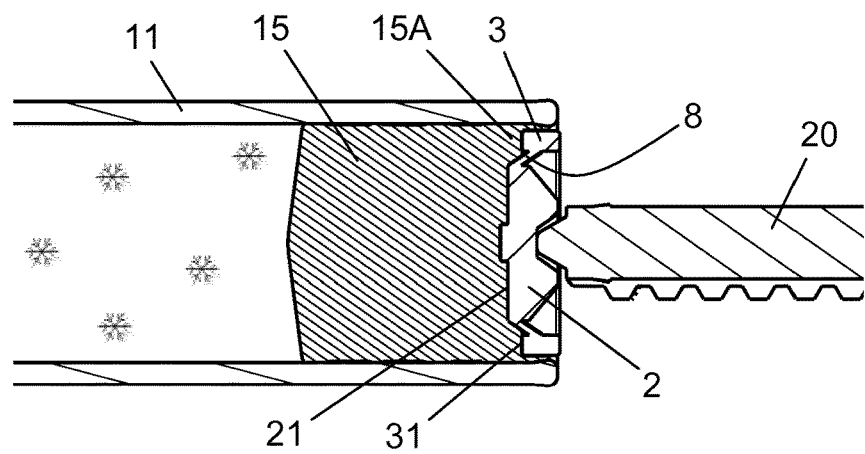
FIG. 5 shows the proximal section of the drug cartridge in frosty conditions after deformation of the piston washer.

FIG. 5 shows what happens if the cartridge 10 is e.g. exposed to frost. In that case, given that the piston rod 20 is supported by a delivery mechanism in the drug delivery device and thus cannot move proximally, the proximally directed force on the piston 15 from the drug expanding in the chamber 14 will force the bridges to deform and the outer portion 3 to displace axially in the proximal direction, thereby allowing the peripheral portion 15A of the piston 15 to crawl up around the centre portion 2 in response. When the force exceeds a certain threshold the bridges 8 begin to yield making permanent room for the drug and providing the needed volume expansion of the chamber 14. Cracking of the cartridge wall 11 is thus avoided.

Figure 6:
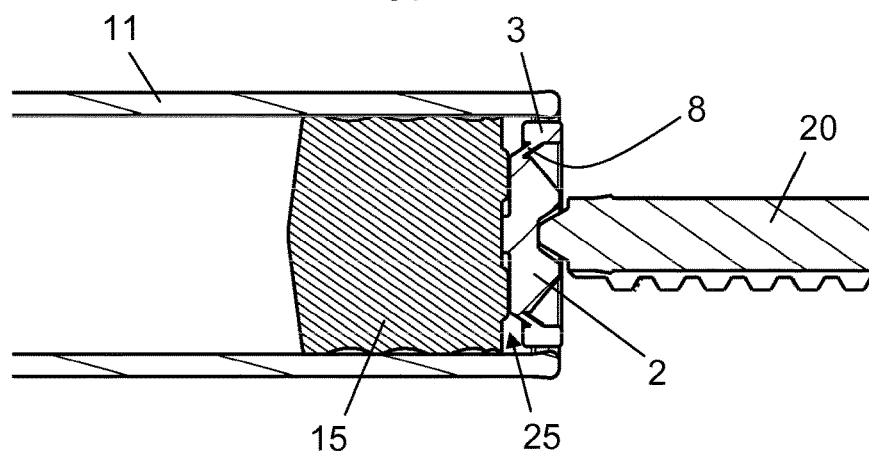
FIG. 6 shows the proximal section of the drug cartridge after thawing of the drug.

FIG. 6 shows the cartridge 10 after thawing of the drug in the chamber 14. The outer portion 3 is permanently displaced relative to the centre portion 2 due to the plastic deformation of the bridges 8, leaving an air gap 25 between the distal surface 31 and the piston 15. Regardless of the usability of the drug the drug delivery device can still be used to administer doses of the drug as before. However, the time to completion of a dose may have increased due to the lacking support on the piston by the outer portion 3.

The axial displacement of the outer portion 3 relative to the centre portion 2 provides a visual indication that the drug has potentially been exposed to frost. Hence, it is possible for an examiner of a customer complaint to verify whether drug freezing may have been a reason for the complaint or not. The exterior surface 23 may be configured to appear visibly different from the exterior surface 33, e.g. by having a different colour, such that the relative displacement of the outer portion 3 and the centre portion 2 is even more clearly identifiable.

Figure 7:
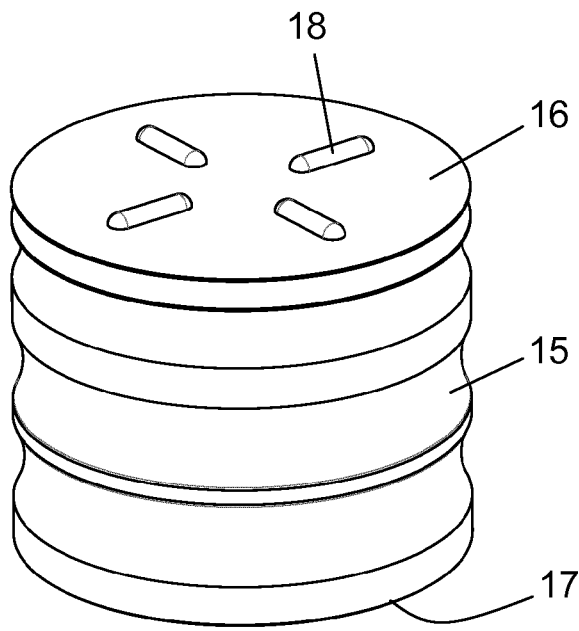
FIG. 7 is a perspective view of a type of piston used in some drug delivery devices.

FIG. 7 is a perspective view of the piston 15. The piston 15 is made of an elastomeric material, e.g. rubber, and extends generally cylindrically between a proximal end face 16 and a distal end face 17. Four short ridges 18 on the proximal end face 16, forming a disrupted cross, are provided to reduce the likelihood of the piston 15 sticking to another piston during storage.

Figure 8:
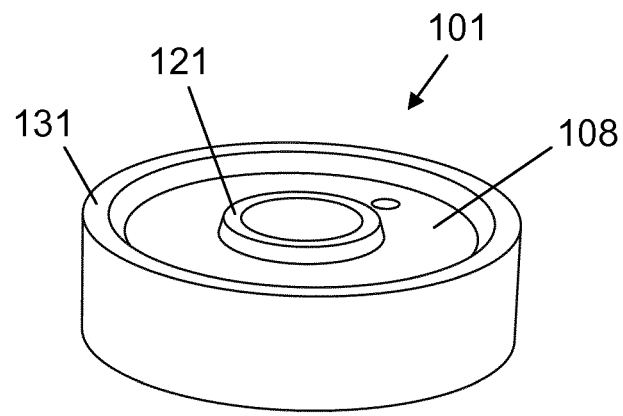
FIG. 8 shows a prior art piston washer.

FIG. 8 is an example of a piston washer 101, which in the prior art has been used with the piston 15. The piston washer 101 has a central push face 121, a peripheral push face 131, and a ring-shaped furrow 108 therebetween to accommodate the ridges 18 in a generally non-compressive manner.

Figure 9:
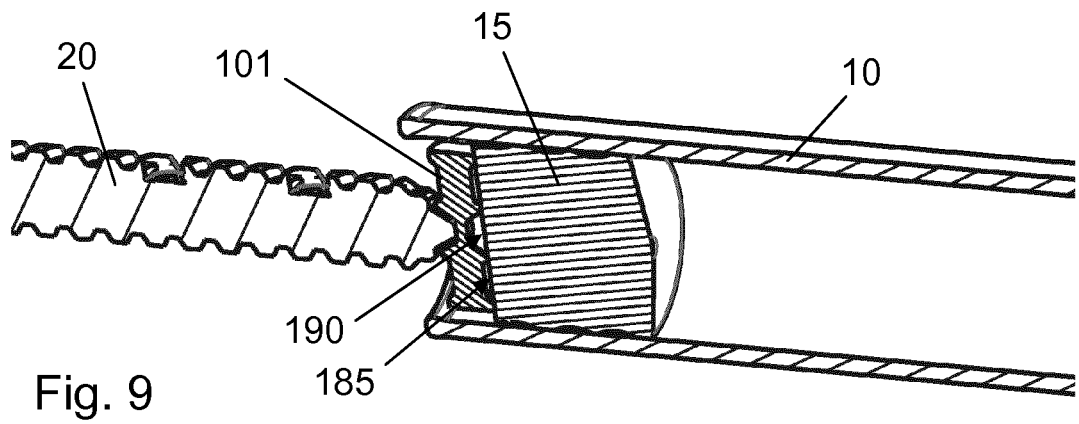
FIG. 9 is a longitudinal section view of the piston washer of FIG. 8 in use.

FIG. 9 is a longitudinal section view of an exemplary set-up of the piston 15 and the piston washer 101 within the generally cylindrical wall of the cartridge 10. The piston washer 101 is arranged between the piston rod 20 and the proximal end face of the piston 15. Due to the configuration of the central push face 121 and the fact that the volume of the furrow 108 is much larger than the accumulated volume of the ridges 18, air pockets 185, 190 are created between the distal end face of the piston washer 101 and the proximal end face of the piston 15. During distal movement of the piston 15 in the cartridge 10 the force from the plunger acting on the piston washer 101 compresses the air trapped in these air pockets 185, 190, and a small compression of the ridges 18 may additionally occur, which all in all increases the relaxation time of the dosing system at the end of the dose expelling.

Figure 10:
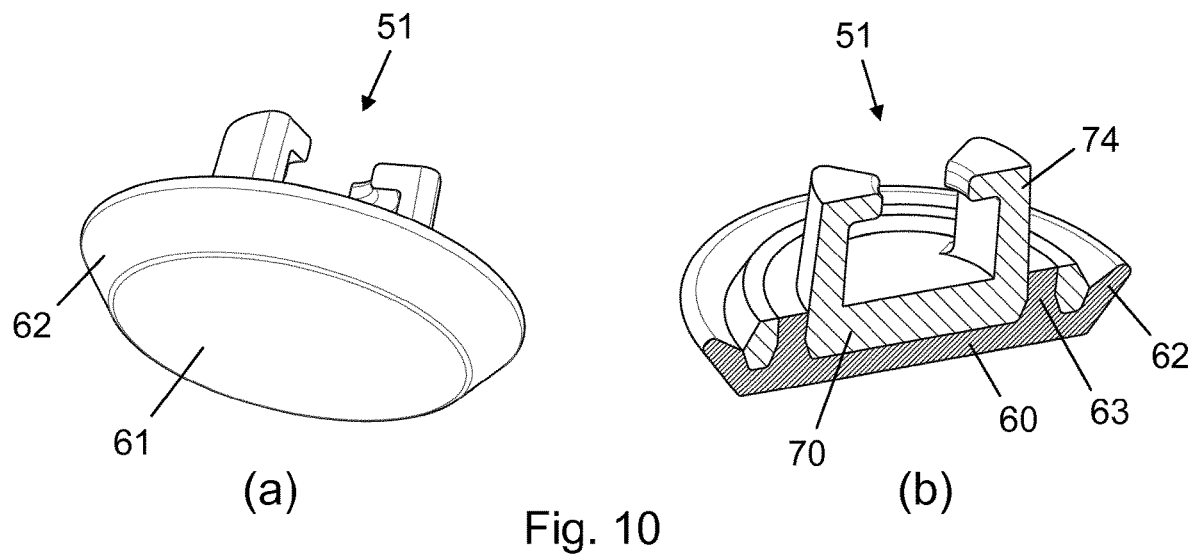
FIGS. 10A and 10B show different views of a piston washer according to another embodiment of the invention before use.

FIG. 10 shows different views of a piston washer 51 according to another embodiment of the invention. FIG. 10a is a perspective distal view of the piston washer 51 before use, showing a planar distal end face 61 and an angled lip 62. FIG. 10b is a cross-sectional perspective view from where it can be seen that the piston washer 51 is a two-part component which comprises a rigid core body 70 and an interface body 60 attached to a distal end thereof by an inner retaining ring 63. The rigid core body 70 comprises a pair of proximally extending fingers 74 for engagement with a piston rod.

Figure 11:
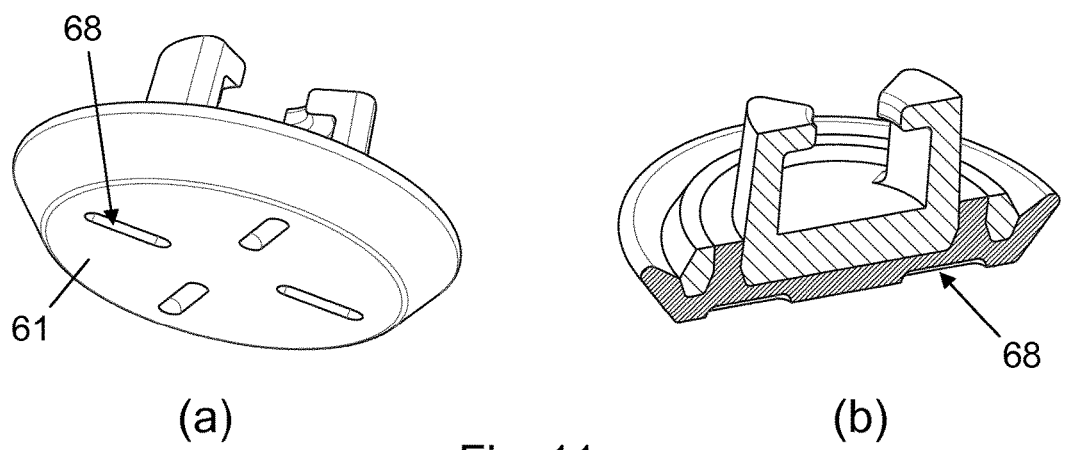
FIGS. 11A and 11B show the piston washer of FIG. 10 after prolonged contact with the piston of FIG. 7.

FIG. 11 shows the piston washer 51 following a prolonged period of time of being in abutment with the piston 15. The interface body 60 is made of a material which is softer than the proximal end surface of the piston 15 and which has a higher compression set than the piston 15. This results in the ridges 18 sinking into the distal end face 61, when the piston washer 51 and the piston 15 are pressed towards one another. The ridges 18 thereby practically avoid deformation themselves. In this particular embodiment the interface body is a TPE having a compression set of about 60%, and when the piston washer 51 and the piston 15 are separated after the period of contact, e.g. four hours, indents 68 are left permanently in the distal end face 61.

Figure 12:
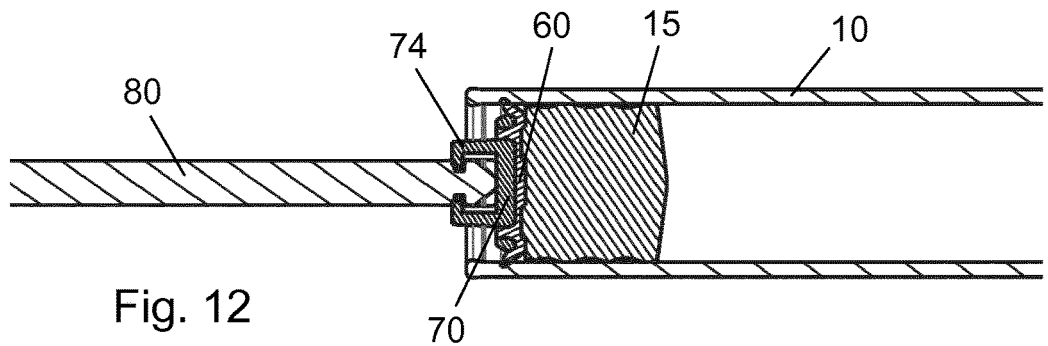
FIG. 12 is a longitudinal section view of the piston washer during use.

In FIG. 12 the piston washer 51 is attached to a piston rod 80 and the interface body is brought into abutment with the piston 15. As can be seen the distal end face 61 conforms completely to the proximal end surface of the piston 15, so no air pockets are established. Furthermore, since the ridges 18 do not deform the whole system comprising the piston rod 80, the piston washer 51, and the piston 15 acts as a stiff construction during dose expelling from the cartridge 10. The relaxation time is thereby significantly reduced, since the elastic recovery of the piston 15 is minimised.

Figure 13:
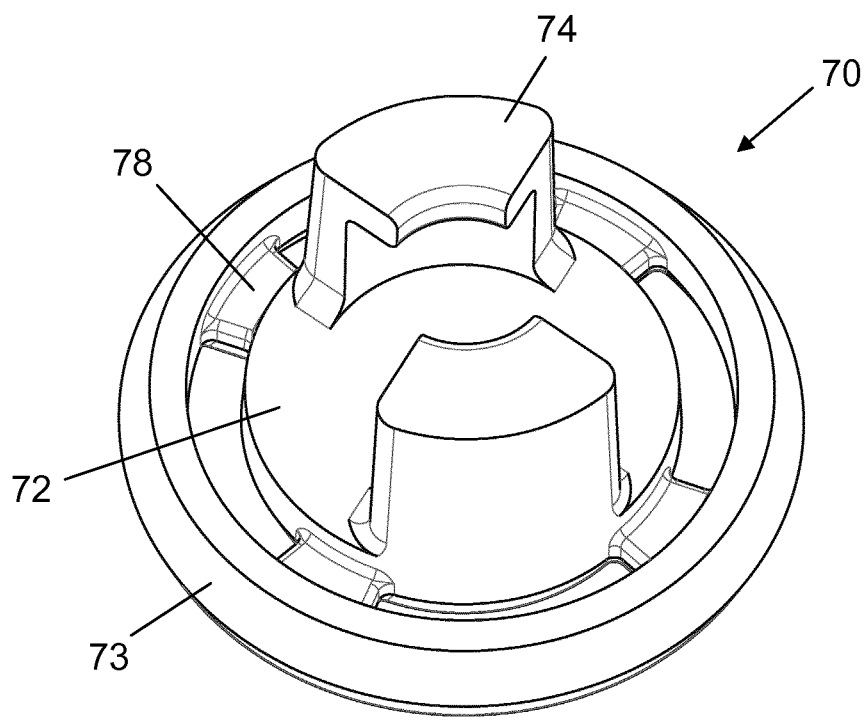
FIG. 13 is a perspective view of a first part of the piston washer.

FIG. 13 is a perspective proximal view of the rigid core body 70, which apart from the pair of fingers 74 has a configuration much similar to that of the piston washer 1 shown in FIG. 1. The rigid core body 70 comprises a central portion 72, which is adapted for abutment with a piston rod, and a peripheral portion 73 radially spaced apart from the central portion 72 by a plurality of radial bridges 78, serving as a deformation zone and being preconfigured to undergo permanent deformation before any other portion of the rigid core body 70, should the drug freeze in the cartridge 10 during use, as described previously.

Figure 14:
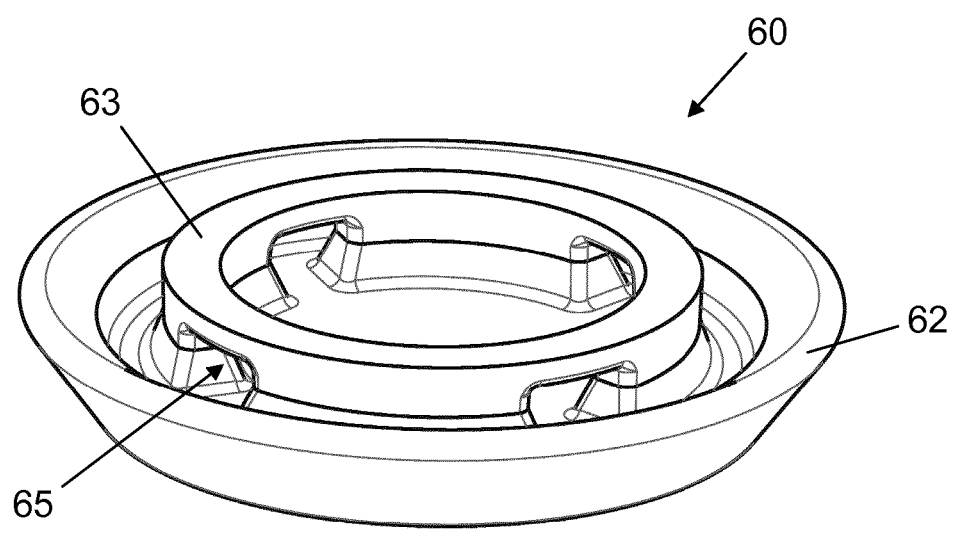
FIG. 14 is a perspective view of a second part of the piston washer.

FIG. 14 is a perspective proximal view of the interface body 60. It is seen that the inner retaining ring 63 has a plurality of radial openings 65 for passage of the plurality of radial bridges 78, ensuring a tight engagement between the two parts of the piston washer 51. The lip 62 may or may not be adapted to seal against the inner wall of the cartridge 10.

The invention claimed is:

1. A piston washer for a drug delivery device, the piston washer comprising:
    a central portion arranged about a centre axis,
    a peripheral portion, and
    an axially pliable structure connecting the central portion and the peripheral portion, the axially pliable structure being preconfigured to undergo permanent deformation in response to a difference between a first resultant force acting on the peripheral portion and a second resultant force acting on the central portion exceeding a threshold level,
wherein the central portion comprises a proximal surface configured for abutment with a piston rod and a distal surface configured for abutment with a piston,
wherein the piston washer is configured to transition permanently by deformation of the axially pliable structure from a first state in which the central portion and the peripheral portion are physically connected and assume a first relative axial position to a second state in which the central portion and the peripheral portion are physically connected and assume a second relative axial position in response to the difference between the first resultant force and the second resultant force transiently exceeding the threshold level, and
wherein the central portion, the peripheral portion and the axially pliable structure are of the same material, thus providing a single component piston washer.

2. A piston washer according to claim 1, wherein the axially pliable structure is configured to exhibit plastic deformation.

3. A piston washer according to claim 1, wherein the central portion and the peripheral portion are radially separated, and the axially pliable structure constitutes a radially extending deformation zone, which is configured to deform before any area of the central portion and the peripheral portion, when the difference between the first resultant force and the second resultant force exceeds the threshold level.

4. A piston washer according to claim 3, wherein the axially pliable structure comprises a plurality of radial bridges, each of the plurality of radial bridges comprising a first end being connected to a radially inwardly directed surface of the peripheral portion and a second end being connected to a radially outwardly directed surface of the central portion.

5. A piston washer according to claim 4, wherein the plurality of radial bridges are evenly distributed along a circumference of the central portion.

6. A piston washer according to claim 1, wherein the axially pliable structure is made of a PP block copolymer.

7. A piston washer according to claim 1, wherein the central portion, the peripheral portion and the pliable structure are of the same material.

8. A piston washer according to claim 1, wherein a segment of the peripheral portion is flexible, and
wherein at least two radially outwardly directed surface portions of the peripheral portion comprises a radially outwardly directed protrusion.

9. A piston washer according to claim 1, wherein at least a distal face of the central portion is covered by a material having a compression set in the range of 55% to 75%.

10. A drug delivery device comprising a piston washer according to claim 1.

11. A drug delivery device according to claim 10, further comprising:
a drug reservoir comprising a chamber defined by
a reservoir body,
a penetrable septum closing a first portion of the reservoir body, and
a piston closing a second portion of the reservoir body, and
a piston rod for moving the piston towards the penetrable septum,
wherein at least a portion of the central portion is arranged between the piston rod and the piston.

12. A drug delivery device comprising:
a drug reservoir comprising a chamber defined by:
a reservoir body,
a penetrable septum closing a first portion of the reservoir body, and
a piston closing a second portion of the reservoir body,
a piston rod for moving the piston towards the penetrable septum, and
a piston washer according to claim 1 being arranged between the piston rod and the piston,
wherein a proximal end portion of the piston comprises a first material having a first hardness and a first compression set, and a distal end portion of the piston washer comprises a second material having a second hardness and a second compression set,
wherein the first material and the second material are arranged to be in, or to enter into, abutment, and
wherein the first hardness is greater than the second hardness and the second compression set is higher than the first compression set.

13. A drug delivery device according to claim 12, wherein the second compression set is in the range of 55% to 75%.

* * * * *